United States Patent [19]

Cammann

[11] Patent Number: 4,834,535
[45] Date of Patent: May 30, 1989

[54] METHOD OF MEASURING ATOMIC SPECTRA COMPENSATING FOR ATOMIC ABSORPTION BY FREQUENCY MODULATION AND USING THE DOPPLER EFFECT

[76] Inventor: Karl Cammann, Amalienstrasse 89, 8000 München 40, Fed. Rep. of Germany

[21] Appl. No.: 41,106
[22] PCT Filed: Jul. 3, 1986
[86] PCT No.: PCT/DE86/00276
  § 371 Date: Feb. 24, 1987
  § 102(e) Date: Feb. 24, 1987
[87] PCT Pub. No.: WO87/00272
  PCT Pub. Date: Jan. 15, 1987

[30] Foreign Application Priority Data
  Jul. 4, 1985 [DE] Fed. Rep. of Germany ....... 3523874
  Jun. 18, 1986 [DE] Fed. Rep. of Germany ....... 3620324

[51] Int. Cl.⁴ .......................... G01J 3/06; G01J 3/32; G01J 3/433
[52] U.S. Cl. .................................... 356/307; 356/308; 356/311
[58] Field of Search ............... 356/307, 308, 326, 328, 356/334, 311

[56] References Cited

U.S. PATENT DOCUMENTS

| | | | |
|---|---|---|---|
| 3,565,567 | 2/1971 | Rains | 356/307 |
| 3,676,004 | 7/1972 | Prugger et al. | 356/307 |
| 3,917,407 | 11/1975 | Newstead | 356/328 |
| 3,957,375 | 5/1976 | Hadeishi | 356/307 |
| 4,264,141 | 4/1981 | Guers et al. | 350/486 |
| 4,341,470 | 7/1982 | Parker et al. | 356/307 |

FOREIGN PATENT DOCUMENTS 918879 2/1963 United Kingdom ................ 356/307

OTHER PUBLICATIONS

Lue "Wavelength Modulating Spectrometer Implemented with Photovoltaic Photodiodes" J. of P. E.:-Scientific Inst., vol. 12#9 Sep. 79, 833–36.
Ballik "Electrostatically Scanned Reflectors For Interferometer & Laser Applications" App. Optics, Jan. 1972, vol. 11 #1 pp. 125–134.
Schedewie et al., "Digital Electroptic Light Beam Deflection used for Spectral Wavelength Modulation" App. Opt. vol. 11 #4, Apr. 1972 pp. 957–958.
Perregaux et al., "A Simple Technique For Wavelength Modulation of Optical Spectra", App. Optics vol. 7 #10, Oct. 1968, pp. 2031–2035.

Primary Examiner—Vincent P. McGraw
Attorney, Agent, or Firm—Lee & Smith

[57] ABSTRACT

In the atomic absorption or atomic fluorescence spectroscopy the problem exists to compensate the background absorption. For this purpose a measuring light beam, which is passed through a sample space, is frequency modulated by using the Doppler effect. This is achieved in that devices for generating a rate of change of the optical path length passing between two points of this path of rays of the measuring light beam (12) are provided in the path of rays of the measuring light beam (12). Different constructional solutions herefor are described. The optical path length can be varied cyclically by movable mirrors. But it is also possible to arrange a crystal (132) in the path of rays, the refractive index of which can be varied cyclically by applying an electric voltage to the field plates. (134 and 146).

21 Claims, 4 Drawing Sheets

METHOD OF MEASURING ATOMIC SPECTRA COMPENSATING FOR ATOMIC ABSORPTION BY FREQUENCY MODULATION AND USING THE DOPPLER EFFECT

Technical Field

The invention relates to the measurement of atomic spectra for the purpose of determining the quantity of a looked-for element, the atoms of which absorb in a narrow spectral range. In particular the invention relates to the problem of background compensation with such measurements.

BACKGROUND ART Atoms emit and absorb in certain narrow spectral ranges (spectral lines). This causes at such wavelengths, which are also emitted by the respective atom. This fact is used to determine the amount or concentration of a looked-for element in the sample. For this purpose the sample is "atomized". It is taken care that the atoms of the looked-for elements are present in atomic state in a sample area. This atomization can occur in a flame. Quite usual is also atomization in a "graphite tube atomizer". With the latter a sample is introduced into a small tube made of graphite, which tube is heated to a high temperature by passing electric current therethrough under inert gas, at this temperature, the sample being decomposed and the atoms forming a "cloud of atoms" in the small graphite tube.

A measuring light beam, the light of which comprises the spectral lines of the looked-for element, among them an absorption line, is directed through such a cloud of atoms or flame. The atoms of the looked-for element absorb such light very strongly, while this measuring light beam theoretically is not influenced by the atoms of the remaining elements of the sample. The lines of the measuring light beam do not correspond to the absorption lines of the other sample elements.

These ideal conditions, however, often are not present. An unspecific absorption, i.e. not caused by the atoms of the looked-for element, occurs, such absorption being called background absorption. This background absorption is due to the elements of the sample not atomized, namely solid particles or molecules absorbing in a wide band. With highly sensitive measurements, this background absorption is a factor not to be neglected and must be compensated.

For this purpose it is known from No. DE-C-1,964,469 to frequency modulate the measuring light beam, which originates from a single radiation source formed as line emitter. According to No. DE-C-1,964,469 this frequency modulation is effected by using the Zeeman effect. If a magnetic field is applied to the line emitting light source, for example a hollow cathode lamp or a high-frequency discharge lamp, a change of the energy level permitted by quantum mechanics of the emitting atoms occurs in the light source. Consequently each emitted spectral line is split into a plurality of lines. In a magnetic field applied transversely to the direction of the measuring light beam, splitting occurs into a central component, which is unshifted relative to the original spectral line but polarized parallel to the direction of the magnetic field, and further into components, which are symmetrically arranged to the central component with respect to wavelengths and are polarized perpendicularly to the direction of the magnetic field. In an arrangement, in which the magnetic field points in the direction of the measuring light beam, the central unshifted component does not appear.

From No. No. DE-A-2,165,106 a method of background compensation in the atomic absorption spectroscopy is known, with which also a frequency modulation of the spectral line emitted from the light source is effected for the purpose of background compensation. No. DE-A-2,156,106 mentions also the Doppler effect as a means for frequency modulating the emission line. But how frequency modulation by means of the Doppler effect is to be realized in practice, is not said in No. DE-A2,156,106. Also this printed publication describes line splitting by means of the Zeeman effect as preferred embodiment.

From No. AU-A-251,689 it is known to scan the profile of a spectral line by means of atomic absorption spectroscopy (AAS) or atomic fluorescence spectroscopy (AFS) by shifting a very narrow emission or absorption line relative to an absorption or emission line respectively, of greater width to be analysed. According to the teaching of No. AU-A-251,689 this frequency shift can be effected by using the Doppler effect, the Zeeman effect or the Stark effect. In an embodiment described in No. U-A-251,689 the partial pressure of a looked-for element in a sample is measured by scanning the absorption lines by applying the Zeeman effect, either to the light source or to the sample and recording two-dimensionally the absorption as function of wavelength, integration being effected throughout the whole wavelength profile for determining the quantity or the partial pressure of the looked-for element.

Also this printed publication does not show in detail how the Doppler effect is to be used for wavelength modulation.

DISCLOSURE OF THE INVENTION

It is the object of the invention to effect a compensation of the background absorption in the atomic absorption or atomic fluorescence spectroscopy by frequency modulation using the Doppler effect.

It is a further object of the invention to improve the informations about the background absorption and thus to permit more exact background absorption.

According to one aspect of the invention a device for measuring atomic spectra for determining the quantity of a looked-for element in a sample is provided, the atoms of this element absorbing in a narrow spectral range (absorption lines). The device comprises atomizing means for atomizing the sample in a sample area such that the looked-for element is present in atomic state in this sample area. Light source means are provided for generating a narrow-band measuring light beam, the wavelengths of which are located at least close by the absorption line and for guiding this measuring light beam through the sample area. Measuring means serve for measuring an optical interaction between measuring light beam and atomized sample and for generating a measuring signal. Furthermore frequency modulation means are provided for frequency modulating the measuring light beam passing through the sample space by using the Doppler effect, such that the overlapping of the wavelength profiles of measuring light beam and absorption line is varied. Signal processing means serve for generating a background compensated measuring value of said quantity of the looked-for element from the varied measuring signal received with the frequency modulation. According to the invention the frequency modulation means comprise means arranged in the path of rays of the measuring light beam for generating a rate of change of the optical path length extending between two points of this path of rays of the measuring light beam.

A periodic change of the optical path length between a maximum value and a minimum value can be caused by the means for generating a temporal change of the optical path length. The means for generating a rate of change of the optical path length may comprise at least one movable reflecting surface. Alternatively the means for generating a rate of change of the optical path length may comprise an optical material arranged in the path of rays of the measuring light beam, which optical material is transparent for the measuring light beam and has a refractive index controllable by an applied control signal, and means for applying a periodic control signal.

Another aspect of the invention relates to a method for measuring the atomic spectra (AAS, AFS) for determining the quantity of a looked-for element in a sample, the atoms absorbing these elements in a narrow spectral range (absorption lines). An atomization of the sample occurs such that the looked-for element is present in atomic state in a sample area. A narrow-band measuring light beam is generated, the wavelength of which is located at least close by the absorption line. This measuring light beam is directed through the sample area. An optical interaction (absorption, fluorescence) is measured between measuring light beam and atomized sample. Thereby a variation of the relative position of the wavelengths of the measuring light beam and of the absorption line occurs for scanning the absorption line by the narrow-band measuring light beam. This variation occurs through a range (scanning range) clearly exceeding the width of the absorption line such that a background absorption spectrum is determined within a well-defined band width beside the absorption line. Said interaction is two-dimensionally recorded as a function of said varied relative position of the wavelengths, namely as an interaction as function of the wavelength. The measurement of said interaction is corrected by a background measuring value obtained from the background absorption spectrum in the range of the absorption line. The profile of the background absorption spectrum can be extrapolated into the range of the absorption line such that also in a background absorption very much dependent on wavelengths a very exact compensation of the background absorption is possible. Furthermore there is the possibility already mentioned in No. AU-A-251,689 to integrate the measured interaction over the absorption line, while each single measured absorption value can be corrected for the extrapolated background absorption. Finally it can be found out, whether irregularities, rotational bands of molecules for example, appear in the background. The measurement can be restricted to a range, which does not contain such irregularities.

Modifications of the invention are subject matter of further claims.

BRIEF DESCRIPTION OF THE DRAWINGS

Some embodiments of the invention will now be described in greater detail hereinbelow with reference to the accompanying drawings.

PREFERRED EMBODIMENTS OF THE INVENTION

Figure 1:
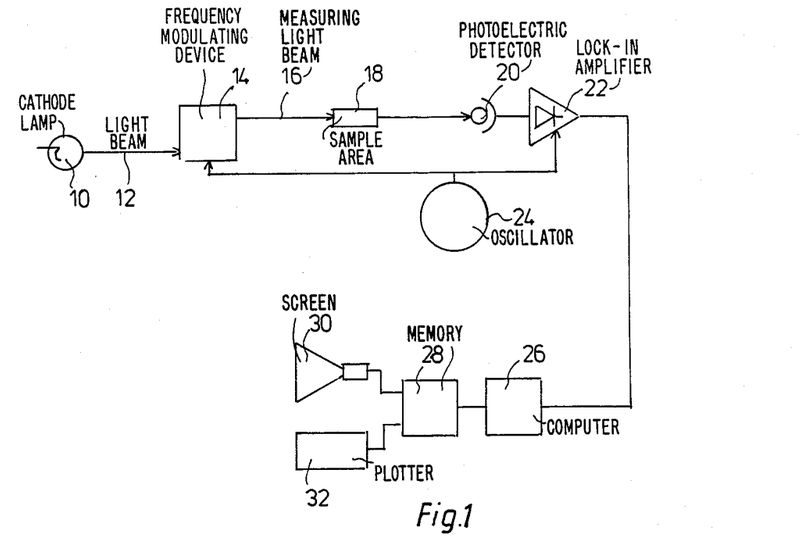
FIG. 1 schematically shows a measuring arrangement for detecting the background absorption in the atomic absorption spectroscopy.

In FIG. 1 a measuring light beam 12 originates from a hollow cathode lamp 10. The measuring light beam 12 is frequency modulated by a frequency modulating device 14 of the type still to be described by using the Doppler effect. The frequency modulated measuring light beam 16 passes through a sample area 18. This sample area can be a known graphite tube atomizer. In the sample area, the sample is present predominantly in atomic state. But a background absorption can occur by solid components and molecules not decomposed. The absorption of the frequency modulated measuring light beam 16 is detected by a photoelectric detector 20, for example a photomultiplier. The output signal of the detector 20 is applied to a lock-in amplifier 22. The lock-in amplifier is controlled by an oscillator 24 together with the frequency modulating device 14. The output signal from the lock-in amplifier 22 is digitized in a computer 26. The digitized output signal is applied to a memory 28 and is stored there as a function of time. The stored output signals are then displayed on a screen 30 or are printed out by a plotter 32.

Figure 2:
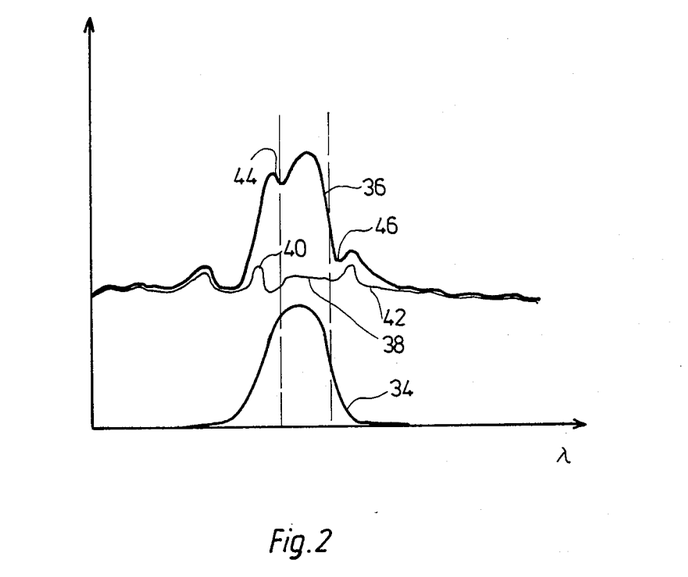
FIG. 2 schematically shows an absorption spectrum with background absorption, the background absorption comprising rotational bands of molecules.

In FIG. 2 numeral 34 shows an absorption spectrum as it would be received if only atoms of a certain looked-for element were in the sample space and no disturbances occurred by background absorption. These idealized conditions are not available in practice. The spectrum has a profile as illustrated by the curve 36, for example. A background absorption is superimposed to the absorption spectrum of the looked-for element, such background absorption being illustrated in curve 38 in FIG. 2. In the illustrated example the background absorption comprises irregularities as illustrated at 40 and 42, which are due to the rotational spectra of the molecules present in the sample space.

By not only measuring the values of the total absorption and the background absorption at certain predetermined wavelengths but observing the curve profile, errors can be avoided which are caused by measuring the background absorption just at a rotational line of a molecule included in the matrix. It has to be noted, that, with highly sensitive measurements, the background absorption can in practice be a multiple of the specific absorption of the looked-for element.

The absorption band of the looked-for element, which here is illustrated relatively strong by curve 34, can well be in the order of magnitude of such irregularities of the background absorption, as they illustrated at 40 and 42. This can be taken into account by studying the signal as a function of wavelength with the frequency modulation of the measuring light beam 16. Such a taking into account can also be effected in a computer by appropriate signal processing. A range about the central wavelength of the absorption band which is located between the nearest irregularities of the curve profile in deviation from an ideal bell curve, here between the points 44 and 46, can be selected for the measurement, for example, as indicated by the broken lines in FIG. 2.

Figure 3:
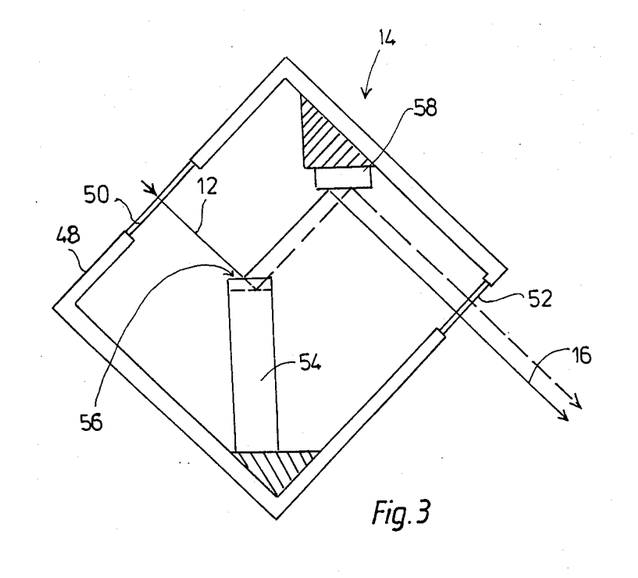
FIG. 3 shows an embodiment of a device for providing a frequency modulation by means of the Doppler effect.

In FIG. 3 an embodiment of a frequency modulating device 14 is illustrated. A housing 48 of rectangular cross section has windows 50 and 52 laterally offset in two opposite side walls. In the housing 48, a vibrator 54 is arranged, which here is formed by a prismatic piezoelectric body, to which a periodic signal at high frequency can be applied (in a way not illustrated). The end face 56 of this vibrator is reflecting. A fixed mirror 58 parallel to the end face is arranged in the housing 48 facing the end face 56. The measuring light beam 12 enters through the window 50 into the housing 48 of the device 14, is reflected by the reflecting end face of the vibrator 54 to the mirror 58 and leaves the housing 48 parallel to the direction of incidence through the window 52 as frequency modulated measuring light beam 16.

As can be seen from FIG. 3, the vibrator 54 changes its length when an electric voltage is applied thereto. Thereby a rate of change of the optical path length of the measuring light beams 12,16 between the windows 50 and 52 is caused. As seen from the sample space this rate of change has the same effect as a corresponding reciprocating movement of the light source, such that a frequency modulation of the measuring light beam 16 occurs due to the Doppler effect.

Figure 4:
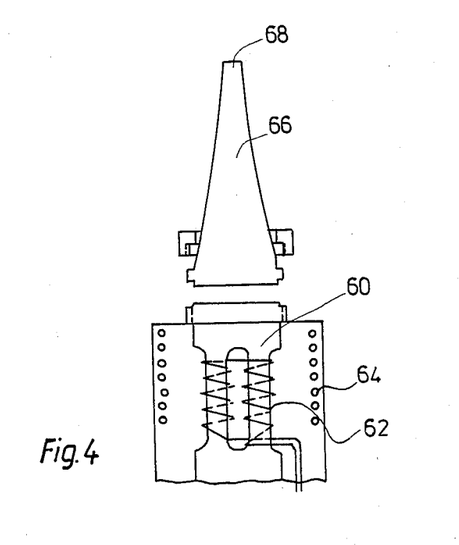
FIG. 4 shows another embodiment of the vibrator in the embodiment of FIG. 3.

In FIG. 4 a modified embodiment of the vibrator is illustrated. A magnetostrictive vibrator 60 having an exciting coil 62 is provided instead of a piezoelectric vibrator 54. A magnetic field is generated by the current flowing through the exciting coil and constricts the magnetostrictive vibrator 60, which can be made of nickel, corresponding to the field intensity. In order to obtain higher amplitudes the arrangement is provided with a cooler 64. An amplitude amplifying tapering body 66 is attached on the vibrator 60, the small end face 68 of this body being reflecting. The reflecting end face 68 replaces the end face 56 of the vibrator 54.

Figure 5:
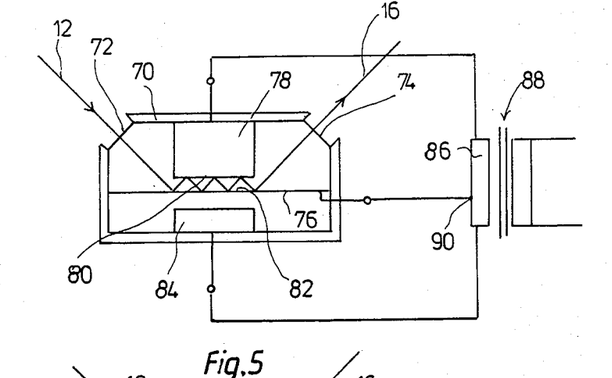
FIG. 5 shows a further embodiment of a device for providing a frequency modulation by means of the Doppler effect.
Figure 6:
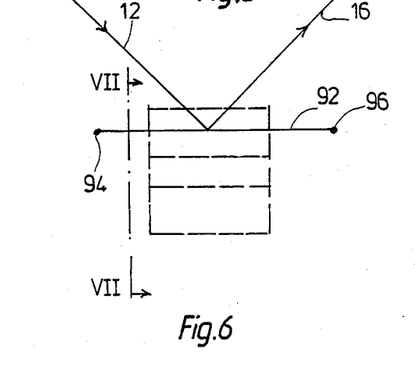
FIG. 6 schematically shows a modification of the movable reflecting surface and its drive.

In the embodiment of FIG. 5 numeral 70 designates a housing, which has an entrance window 72 and exit window 74. A thin diaphragm 76 reflecting at its upper surface in FIG. 5 is clamped into the housing. A capacitor plate 78 in the form of a block with a reflecting underside 80 is located above the diaphragm. The upper side of the diaphragm 76 in FIG. 6 is also provided with a reflecting surface. The measuring light beam 12 enters through the entrance window 72 into the housing 70, is reflected several times between the reflecting layers 80 and 82 of the capacitor plate 78 and the diaphragm 76 and leaves the housing 70 as frequency modulated measuring light beam 16 through the exit window 74. In FIG. 6 a further capacitor plate 84, also in the form of a block, is arranged below the diaphragm. Both of the capacitor plates 78 and 84 are connected to the ends of the secondary winding 86 of a push-pull transformer 88. The diaphragm 76 is connected to the central tap 90 of the push-pull transformer 88.

When the push-pull &transformer 88 is excited by an alternating voltage of relatively high frequency an electric alternating field will act on the diaphragm 76, whereby the diaphragm is caused to vibrate correspondingly. The evacuation of the housing 70 ensures, that these vibrations are not damped by the air in the housing. Due to the vibrations periodic rates of change of the optical path length between the windows 72 and 74 will be observed. This causes a frequency shift in the measuring light beam 16 due to the Doppler effect. The Doppler effect is multiplied because of the measuring light beam being reflected several times at the movable reflecting surfaces formed by the reflecting layer 82.

Figure 7:
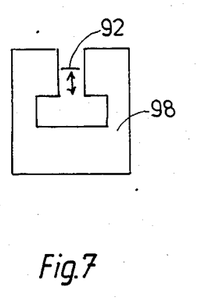
FIG. 7 is a side-elevation of FIG. 6.

In the embodiment of FIGS. 6 and 7 a tape 92 serves as movable reflecting surface, which tape is either metallic or is made of a metal-coated plastic foil. An alternating current of high frequency is passed through this tape through terminals 94 and 96. The tape 92 is located in the air gap of a magnet 98, as can be seen from FIG. 7. Thereby the tape is caused to vibrate, as indicated by the double arrow in FIG. 7. The tape 92 acts as movable reflecting surface, on which the measuring light beam 12 or 16 respectively, is directed.

Figure 8:
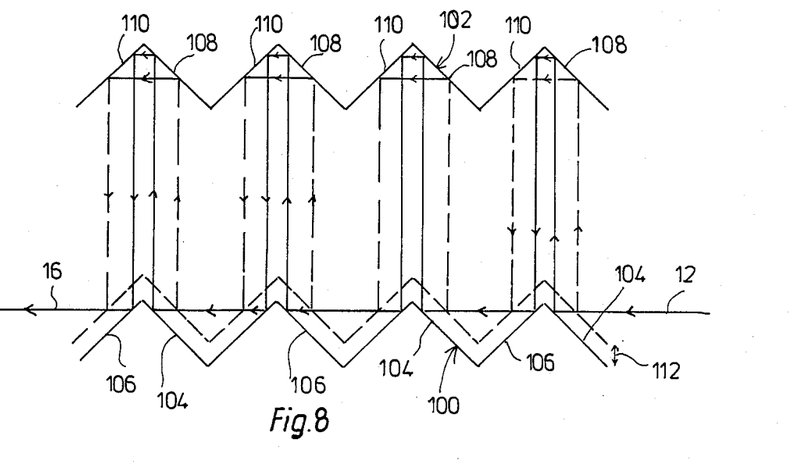
FIG. 8 schematically shows a further embodiment of a device for providing a frequency modulation by means of the Doppler effect.

FIG. 8 shows an arrangement, in which a movable mirror carrier 100 and a fixed mirror carrier 102 are provided. The movable mirror carrier has a plurality of mirrors 104, which are inclined at an angle of 45° to the direction of incidence of the measuring light beam 12, and a plurality of mirrors 106, which are adjacent to the mirrors 104 and form an angle of 225° with the direction of incidence of the measuring light beams 12. Thus the mirrors 104 and 106 of the mirror carrier 100 form a zigzag-shaped mirror arrangement. Accordingly the fixed mirror carrier 102 comprises mirrors 108, which are located parallel to the mirrors 104 and mirrors 110, which are arranged parallel to the mirrors 106. Also the mirrors 108 and 110 are adjacent each other and form right angles. The movable mirror carrier 100 makes an oscillating movement, as illustrated by the double arrow 112.

As can be seen from FIG. 8, the measuring light beam 112 is reflected by 90. by the first mirror 104, then is reflected by two adjacent mirrors 108 and 110 of the fixed mirror carrier 102, subsequently by two mirrors 106 and 104 of the movable mirror carrier etc. until the measuring light beam 12 finally is reflected again as frequency modulated measuring light beam 16 by the last mirror 106 of the movable mirror carrier 100 into the direction of incidence.

As can be seen from the position of the movable mirror carrier 100 shown in dashed lines and the associated path of rays, a periodic change of the optical path length between the entrance point and the exit point occurs and results in a frequency shift by means of the Doppler effect. Also here the Doppler effect is multiplied due to multiple reflections at the movable mirror carrier 100.

Figure 9:
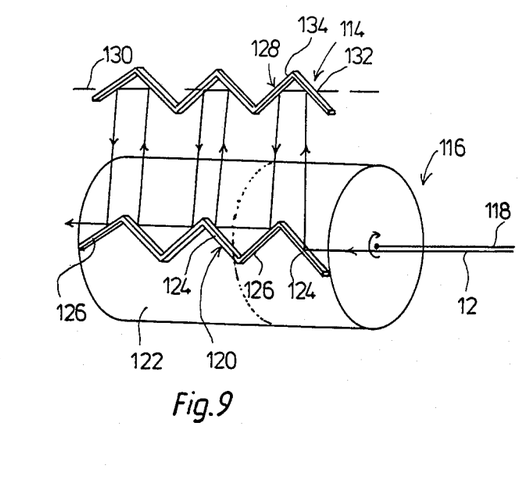
FIG. 9 schematically shows a preferred modification of FIG. 8, wherein frequency modulation by means of the Doppler effect is achieved by a rotating mirror carrier.
Figure 10:
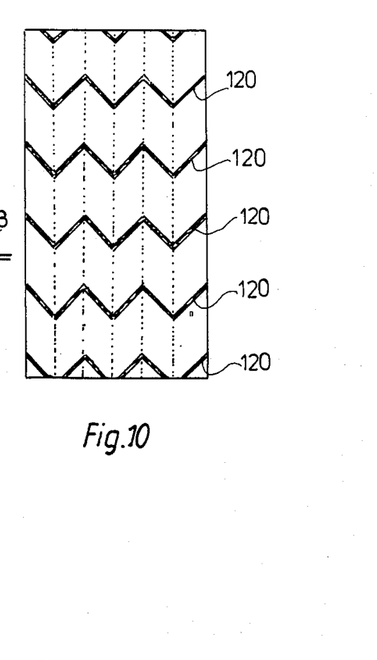
FIG. 10 is a developed view of the lateral area of the mirror carrier of FIG. 9.

In the embodiment according to FIGS. 9 and 10 the means for generating a rate of change of the optical path length comprise a fixed mirror carrier 114 and a mirror carrier 116 rotating relatively to the fixed mirror carrier 114. The mirror carriers have, as still will be explained, reflecting surfaces, the measuring light beam 12 being guided via the reflecting surfaces of the rotating and the fixed mirror carriers 16 or 14, respectively. The reflecting surfaces are arranged such that during rotation the measuring light beam 12 periodically undergoes a rate of change of the optical path length during first time periods and is transmitted uninfluenced during second time periods. For this purpose the measuring light beam 12 is incident in parallel to the circumferential axis 118 of the rotating mirror carrier 116, the movable mirror surfaces of which are arranged at 45° to the rotational axis and are always perpendicular to the cylinder surface. The rotating mirror carrier 116 has a generally elongated cylindrical shape. A plurality of mirror sequences 120 are arranged on the periphery of the rotating mirror carrier 116 as movable reflecting surfaces, of which only one is illustrated in FIG. 9 for simplicity. The mirror sequences 120 extend along a generating line of the cylinder. As can be seen from the developed view of FIG. 10, the mirror sequences are spaced in the circumferencial direction. Each mirror sequence consists (similar to the arrangement of FIG. 8) of a plurality of mirrors 124, 126, which are adjacent to each other and form alternating angles of 45° and 225° with a generating line of the cylinder 122. The fixed mirror carrier 114 has a mirror sequence 128 as fixed reflecting surfaces. The mirror sequence extends along a notional line 130 extending parallel to the axis of rotation 118 of the rotating mirror carrier 116. It consists, similar to the fixed mirror carrier 102 of FIG. 8, of a plurality of mirrors 132,134, which are adjacent to each other and form alternating angles of 45° and 225° with said notional line 130.

The measuring light beam is reflected by a first mirror 124 of a mirror sequence 120 of the rotating mirror carrier 116 to a mirror 132 of the fixed mirror carrier 114 during the first time intervals. Then it is subjected alternating to two reflections each by the mirrors 132,134 of the fixed mirror carrier 114 and the mirrors 126,124 of the rotating mirror carrier 116. Finally it is reflected by a last mirror 126 of the mirror sequence 120 of the rotating mirror carrier 116 into a direction parallel to the axis of rotation 118. The path of rays is similar to the arrangement of FIG. 8. However no vibrating movement of the movable mirror carrier 120 occurs but a rotational movement. During the second time intervals the measuring light beam 112 passes straight through between the mirror sequences 120 of the rotating mirror carrier 116.

Figure 11:
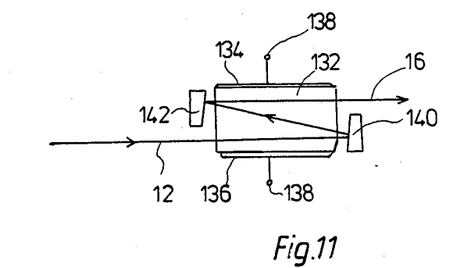
FIG. 11 schematically shows a further preferred embodiment of a device for providing frequency modulation by means of the Doppler effect, a change of the optical path length being caused by a material, the refractive index of which is variable by an applied voltage.

FIG. 11 shows a preferred embodiment of the present invention. In this embodiment a crystal, LiNbO. for example, is arranged in the path of rays of the measuring light beam 12 or 16, respectively. The crystal 132 is arranged between two field plates 134 and 136, which are connected with terminals 138 or 140, respectively. The measuring light beam 12 passes through the crystal 132, is reflected again by a fixed mirror 140 into the crystal 132 and impinges upon a fixed mirror 142, which is arranged on the side of the entrance near the incident measuring light beam 12. The measuring light beam is directed again through the crystal 132 by the mirror 142 and leaves the crystal as measuring light beam 16. Thus the measuring light beam is passed several times through the crystal 132 in a Z-shaped path of rays.

The material of the crystal 132 has an electro-optical characteristic, which is known per se:

If an electrical field is applied to the terminals 138, the refractive index in the crystal 132 changes proportionally to the field intensity. If a delta- or sinus alternating voltage is applied in the range of megacycles per second, the refractive index in the crystal varies correspondingly quickly. This causes a correspondingly rate of change of the optical path length in the crystal 132. The optical path length is defined as product of geometric distance and refractive index of the medium, in which the light proceeds. When the refractive index is changed correspondingly quickly then a high rate of change of the optical path length results, what corresponds to a quick mirror movement. Also here a frequency shift occurs by the Doppler effect. This is achieved without any mechanical movement.

I claim:

1. Method of measuring atomic spectra (AAS,AFS) for the purpose of determining the quantity of a looked-for element, the atoms of which absorb in a narrow spectral range (absorption line), comprising the method steps of
   (a) atomizing the sample such that the looked-for element is present in atomic state in a sample area,
   (b) generating a narrow-band measuring light beam, the wavelengths of which are located at least close by the absorption line,
   (c) directing the measuring light beam through the sample area,
   (d) measuring an optical interaction (absorption, fluorescence) between measuring light beam and atomized sample,
   (e) varying the relative positions of the wavelengths of the measuring light beam and the absorption line for scanning the absorption line by the narrow-band measuring light beam and
   (f) two-dimensionally recording said interaction as a function of said varied relative positions of the wavelengths,
wherein
   (g) the variation of the relative positions of the wavelengths of the measuring light beam is effected through a range (scanning range) clearly exceeding the width of the absorption line such that a background absorption spectrum is determined through a defined band width beside the absorption line and
   (h) the measurement of said interaction is corrected by a background measuring value obtained from the background absorption spectrum in the range of the absorption line.

2. Method as set forth in claim 1, wherein the background measuring value is formed as average value of said interaction through the portions of the scanning range located outside the absorption line.

3. Method as set forth in claim 1, wherein
   (a) a maximum of said two-dimensionally registered interaction is determined as measure of the quantity of the looked-for element in the sample and
   (b) is corrected by the background measuring value.

4. Method as set forth in claim 1, wherein the variation of the relative positions of the wavelengths of measuring light beam and absorption line is effected by frequency modulation of the measuring light beam by means of the Doppler effect.

5. Device for measuring atomic spectra (AAS,AFS) for the purpose of determining the quantity of a looked-for element, the atoms of which absorb in a narrow spectral range (absorption line), in a sample, comprising:
   (a) atomizing means for atomizing the sample in a sample area such that the looked-for element is present in atomic state in this sample area (18),
   (b) light source means (10) for generating a narrow-band measuring light beam, the wavelength of which is located at least close by the absorption line and for directing this measuring light beam through the sample area (18),
   (c) measuring means (20) for measuring an optical interaction between measuring light beam and atomized sample and for generating a measuring signal,
   (d) frequency modulation means (14) for frequency modulating the measuring light beam passing through the sample area using the Doppler-effect such that the overlap of the wavelength profiles of measuring light beam and absorption line is varied and
   (e) signal processing means (26,28) for generating a background compensated measuring value of said quantity of the looked-for element from the varied measuring signal obtained in the frequency modulation,
wherein
   (f) the frequency modulation means (14) comprise means arranged in the path of rays of the measuring light beam (12,16) for generating a rate of change of the optical path length traversed by the measuring light beam (12,16) between two points of this path of rays, and
   (g) the variation of the relative positions of the wavelengths of the measuring light beam is effected through a range (scanning range) clearly exceeding the width of the absorption line such that a background absorption spectrum is determined through a defined band width beside the absorption line.

6. Device as set forth in claim 5, wherein the means (14) for generating a rate of change of the optical path length are arranged to cause a cylclic variation of the optical path length between a maximum value and a minimum value.

7. Device as set forth in claim 6, wherein the means (14) for generating a rate of change of the optical path length comprise at least one movable reflecting surface (56,68,82,92,104,106, 124,126).

8. Device as set forth in claim 6, wherein the means for generating a rate of change of the optical path length comprise
   (a) an optical material (132) arranged in the path of rays of the measuring light beam (12) and transparent for the measuring light beam and having a refractive index controllable by a control signal applied thereto and
   (b) means (134,136) for applying a cyclic control signal to this material (132).

9. Device as set forth in claim 8, wherein the refractive index of the material (132) is variable by a signal applied thereto.

10. Device as set forth in claim 9, wherein the path of rays of the measuring light beam is passed several times through the material (132), which has a variable refractive index, by mirrors (142,140) which are arranged on the entrance side and the exit side of the material (132).

11. Device as set forth in claim 7, wherein the means for generating a rate of change of the optical path length comprise
   (a) a first reflecting surface (56), which is arranged on the end face of a vibrator (54) and to which the measuring light beam (12) is directed, and
   (b) a fixed second reflecting surface (58) parallel to the first reflecting surface, the measuring light beam (12) being reflected to the second reflecting surface by the first reflecting surface (56).

12. Device as set forth in claim 11, wherein the vibrator (54) is a piezoelectric vibrator, which is arranged to be excited by a cyclic voltage.

13. Device as set forth in claim 11, wherein the vibrator is a magetostrictive vibrator (60).

14. Device as set forth in claim 13, wherein an amplitude amplifying tapering body (66) is attached on the vibrator (60), the small end face of the body carrying the first reflecting surface.

15. Device as set forth in claim 7, wherein the means (14) for generating a rate of change of the optical path length comprise
   (a) a fixed reflecting surface (80),
   (b) a diaphragm (78) parallel to the fixed reflecting surface (80) and provided with a reflecting layer (82) facing the fixed reflecting surface, and
   (c) excitation means for generating electrostatic alternating forces between reflecting surface (80) and diaphragm (82),
   (d) the measuring light beam (12) being reflected several times between the reflecting surface (80) and the reflecting layer (82) of the diaphragm.

16. Device as set forth in claim 15, wherein the excitation means comprise
   (a) a first capacitor plate (78), which carries the fixed reflecting surface (80), and
   (b) a second capacitor plate (84), which is arranged on the side of the diaphragm (76) remote from the first capacitor plate (78), and
   (c) a push-pull transformer (88), the ends of which are connected to the capacitor plates (78,84) and the center tap (90) of which is connected to the diaphragm (76).

17. Device as set forth in claim 7, wherein that the movable reflecting surface is formed by an electroconductive reflecting tape (92), which is passed through by an alternating current and is arranged between the poles of a magnet (98).

18. Device as set forth in claim 15, wherein the fixed and movable reflecting surfaces with excitation means for the latter are arranged in a housing (70), which is provided with windows (72,74) for the passage of the measuring light beam (12,16).

19. Device as set forth in claim 7, wherein
   (a) the means for generating a rate of change of the optical path length comprise
      a fixed mirror carrier (114) and
      a mirror carrier (116) rotating relatively to the fixed mirror carrier,
   (b) the mirror carriers (114,116) have reflecting surfaces (132,134 or 124,126, respectively), the measuring light beam (12), being guided via the reflecting surfaces of the rotating and the fixed mirror carriers (116, 114),
   (c) the reflecting surfaces (132,134,124,126) are arranged such that during the rotation the measuring light beam (12) cyclically undergoes a rate of change of the optical path length during first time intervals and is transmitted uninfluenced during second time intervals.

20. Device as set forth in claim 19, wherein
(a) the measuring light beam is incident in parallel to the axis of rotation (118) of the rotating mirror carrier (116),
(b) the rotating mirror carrier (116) has a generally elongated cylindrical shape,
(c) a plurality of mirror sequences (120) are arranged on the periphery of the rotating mirror carrier (116) as movable reflecting surfaces, which mirror sequences each extend along a generating line of the cylinder (122), which are spaced in circumferential direction, and which each consists of a plurality of mirrors (124,126), which are adjacent to each other and form alternating angles of 45° and 225° with the generating line, (d) the fixed mirror carrier (114) has a mirror sequence (128) as fixed reflecting surface, which mirror sequence extends along a notional line (130) extending parallel to the axis of rotation (118) of the rotating mirror carrier (116), which consists of a plurality of mirrors (132,134), which are adjacent to each other and form alternating angles of 45° and 225° with said notional line (130), (e) the measuring light beam (12)
is reflected by a first mirror (124) of a mirror sequence (120) of the rotating mirror carrier (116) to a mirror (132) of the fixed mirror carrier (114) during the first time intervals, then undergoes alternating two reflections each at mirrors of the fixed and the rotating mirror carrier (114 or 116, respectively) and finally is reflected by a last mirror (126) of the mirror sequence (120) of the rotating mirror carrier (116) into a direction parallel to the axis of rotation (118) and the measuring light beam (12) passes straight through between the mirror sequences (120) of the rotating mirror carriers (116) during the second time intervals.

21. Device as set forth in claim 7, wherein
(a) a fixed mirror carrier (102) has fixed reflecting surfaces (108,110), which form a right angle with each other,
(b) a movable mirror carrier (100) has movable reflecting surfaces (104,106), which are facing the fixed reflecting surfaces (108,110) and form an angle of 270° with each other,
(c) the measuring light beam (12) is alternately reflected twice at reflecting surfaces (106, 104) of the movable and twice at reflecting surfaces (108,110) of the fixed mirror carrier (102) and
(d) the movable mirror carrier (100) can be excited to oscillate relative to the fixed mirror carrier (102).

* * * * *